(12) United States Patent
Russell et al.

(10) Patent No.: US 7,535,989 B2
(45) Date of Patent: May 19, 2009

(54) XRF SYSTEM WITH NOVEL SAMPLE BOTTLE

(75) Inventors: Ronald H. Russell, Londonderry, NH (US); Peter John Hardman, Woburn, MA (US); Bradley Hubbard-Nelson, Concord, MA (US)

(73) Assignee: Innov-X Systems, Inc., Woburn, MA (US)

( * ) Notice: Subject to any disclaimer, the term of this patent is extended or adjusted under 35 U.S.C. 154(b) by 288 days.

(21) Appl. No.: 11/582,038

(22) Filed: Oct. 17, 2006

(65) Prior Publication Data

US 2008/0089474 A1    Apr. 17, 2008

(51) Int. Cl.
G01N 23/223    (2006.01)

(52) U.S. Cl. .......................................... 378/44; 378/79

(58) Field of Classification Search ............. 378/44–50, 378/42, 208, 79; 422/58, 67
See application file for complete search history.

(56) References Cited

U.S. PATENT DOCUMENTS

| | | | |
|---|---|---|---|
| 3,378,684 A * | 4/1968 | Mentink et al. ............. | 250/428 |
| 4,599,741 A | 7/1986 | Wittry | |
| 4,848,590 A | 7/1989 | Kelly | |
| 5,236,092 A | 8/1993 | Krotkov et al. | |
| 5,260,576 A | 11/1993 | Sommer, Jr. et al. | |
| 5,314,071 A | 5/1994 | Christian et al. | |
| 5,414,195 A | 5/1995 | Peterson et al. | |
| 5,424,959 A | 6/1995 | Reyes et al. | |
| 5,481,109 A | 1/1996 | Ninomiya et al. | |
| 5,563,929 A | 10/1996 | Connolly et al. | |
| 5,570,406 A | 10/1996 | Komatani | |
| 5,657,363 A | 8/1997 | Hossam et al. | |
| 5,663,997 A | 9/1997 | Willis et al. | |
| 6,266,390 B1 | 7/2001 | Sommer, Jr. et al. | |
| 6,519,315 B2 | 2/2003 | Sommer, Jr. et al. | |
| 6,859,517 B2 | 2/2005 | Wilson et al. | |
| 6,888,917 B2 | 5/2005 | Sommer, Jr. et al. | |
| 7,099,433 B2 | 8/2006 | Sommer et al. | |
| 2003/0053589 A1 | 3/2003 | Ikeshita et al. | |
| 2005/0078786 A1 | 4/2005 | Sommer, Jr. et al. | |
| 2006/0013360 A1 | 1/2006 | Sommer, Jr. et al. | |
| 2006/0262900 A1 | 11/2006 | Sipila et al. | |
| 2007/0030953 A1 | 2/2007 | Sommer et al. | |

FOREIGN PATENT DOCUMENTS

| | | |
|---|---|---|
| CA | 1110996 | 10/1981 |
| EP | 0960092 | 12/1983 |
| JP | 01156646 A | 6/1989 |
| JP | 403216532 A * | 9/1991 |
| SU | 952384 | 12/1979 |

(Continued)

*Primary Examiner*—Hoon Song
(74) *Attorney, Agent, or Firm*—Iandiorio Teska & Coleman

(57) ABSTRACT

An XRF system including an analyzer with a sample bottle holder, an x-ray source positioned to emit x-rays into a sample bottle placed in the holder, and a detector positioned to receive x-rays emitted by a sample in the sample bottle positioned in the sample bottle holder. A supply of sample bottles receivable in the sample bottle holder, each sample bottle including a first cap with the window therein for allowing x-rays to pass there through when the sample bottle is positioned in the holder, and a second cap without a window for transporting and storing the sample.

12 Claims, 9 Drawing Sheets

FOREIGN PATENT DOCUMENTS

| WO | WO 2001/022072 A1 | 3/2001 |
| WO | WO 2005/086616 A2 | 9/2005 |
| WO | WO 2006/094061 A1 | 9/2006 |
| WO | WO 2007/089362 A2 | 8/2007 |
| WO | WO 2008/017075 A2 | 2/2008 |

* cited by examiner

XRF SYSTEM WITH NOVEL SAMPLE BOTTLE

FIELD OF THE INVENTION

This subject invention relates to x-ray fluorescence systems and techniques.

BACKGROUND OF THE INVENTION

Fluids are often analyzed by x-ray fluorescence instrumentation and techniques in a laboratory. Typically, a cup is filled with a sample and an x-ray source beneath the cup directs x-rays into the cup through the bottom. A detector also typically located below the cup receives x-rays emitted by the sample. An analyzer, responsive to the detector, processes the output signals provided by the detector and divides the energy levels of the detected x-ray photons into several energy sub-ranges by counts of the number x-ray photons detected to produce a graph depicting the x-ray spectrum of the sample.

In some environments, a typical XRF analyzer is not suitable. One example is the analysis of fuels and oils on board a marine vessel to check for the presence of contaminants. If the cup tips and/or breaks, the sample will spill onto and damage the x-ray source, the detector, and perhaps the other electronic components and electrical connections of the analyzer unit. Given that the analysis would be performed by personnel who are not scientists on board marine vessels, spillage and breakage as described is likely.

SUMMARY OF THE INVENTION

It is therefore an object of this invention to provide a new more rugged and robust XRF system.

It is a further object of this invention to provide such a system which prevents spillage onto the sensitive components of the XRF analyzer.

It is a further object of this invention to provide such a system which allows for the collection, transport, analysis, and storage of a sample all in one container.

It is a further object of this invention to provide such a system which is easy to use and ergonomic in design.

The subject invention results from the realization that by providing a sample bottle engineered with both a windowed cap and a regular cap and by designing the XRF analyzer to receive the sample bottle fitted with the windowed cap horizontally, then even if spillage occurs from the sample bottle, the sensitive components of the analyzer unit will not be damaged and, in addition, one bottle can be used both for analysis and also for storage and transport.

The subject invention, however, in other embodiments, need not achieve all these objectives and the claims hereof should not be limited to structures or methods capable of achieving these objectives.

This invention features an XRF system including an analyzer with a sample bottle holder, an x-ray source positioned to emit x-rays into a sample bottle placed in the holder, and a detector positioned to receive x-rays emitted by a sample in the sample bottle positioned in the sample bottle holder. A supply of sample bottles is receivable in the sample bottle holder, each sample bottle including a first cap with the window therein for allowing x-rays to pass there through when the sample bottle is positioned in the holder, and a second cap without a window for transporting and storing the sample.

In a preferred embodiment, the sample bottle holder disposes the sample bottle horizontally with respect to the analyzer. The window may include a film surrounded by a gasket receivable under an opening in the cap. The film may be made of Kapton. The bottle and the caps may be made of plastic. The system may include a tray beneath the sample bottle holder for catching any sample spilled from the sample bottle. The preferred sample bottle holder includes a member biased to engage the first cap which has a radiused capture feature designed to interlock the first cap with the sample bottle holder via the biased member.

This invention also features an XRF analyzer sample container system including a bottle for holding a sample to be analyzed by an XRF analyzer, a first cap for an open end of the bottle including a window for allowing x-rays to pass there through when the sample bottle is placed in the XRF analyzer, and a second cap for the open end of the bottle without a window for transporting and storing the sample.

This invention further features an XRF analyzer sample container system including a bottle for holding a sample to be analyzed by an XRF analyzer, and a first cap for the bottle including an opening in the cap, and a film across the opening to allow x-rays to pass through the sample bottle when it is placed in an XRF analyzer.

In a preferred embodiment, the bottle may include a second cap without a window for transporting and storing a sample in the bottle.

This invention also features an XRF analyzer sample container system including a bottle for holding a sample to be analyzed by an XRF analyzer, and a first cap for an open end of the bottle including a window therein for allowing x-rays to pass there through when the sample bottle is placed in the XRF analyzer.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
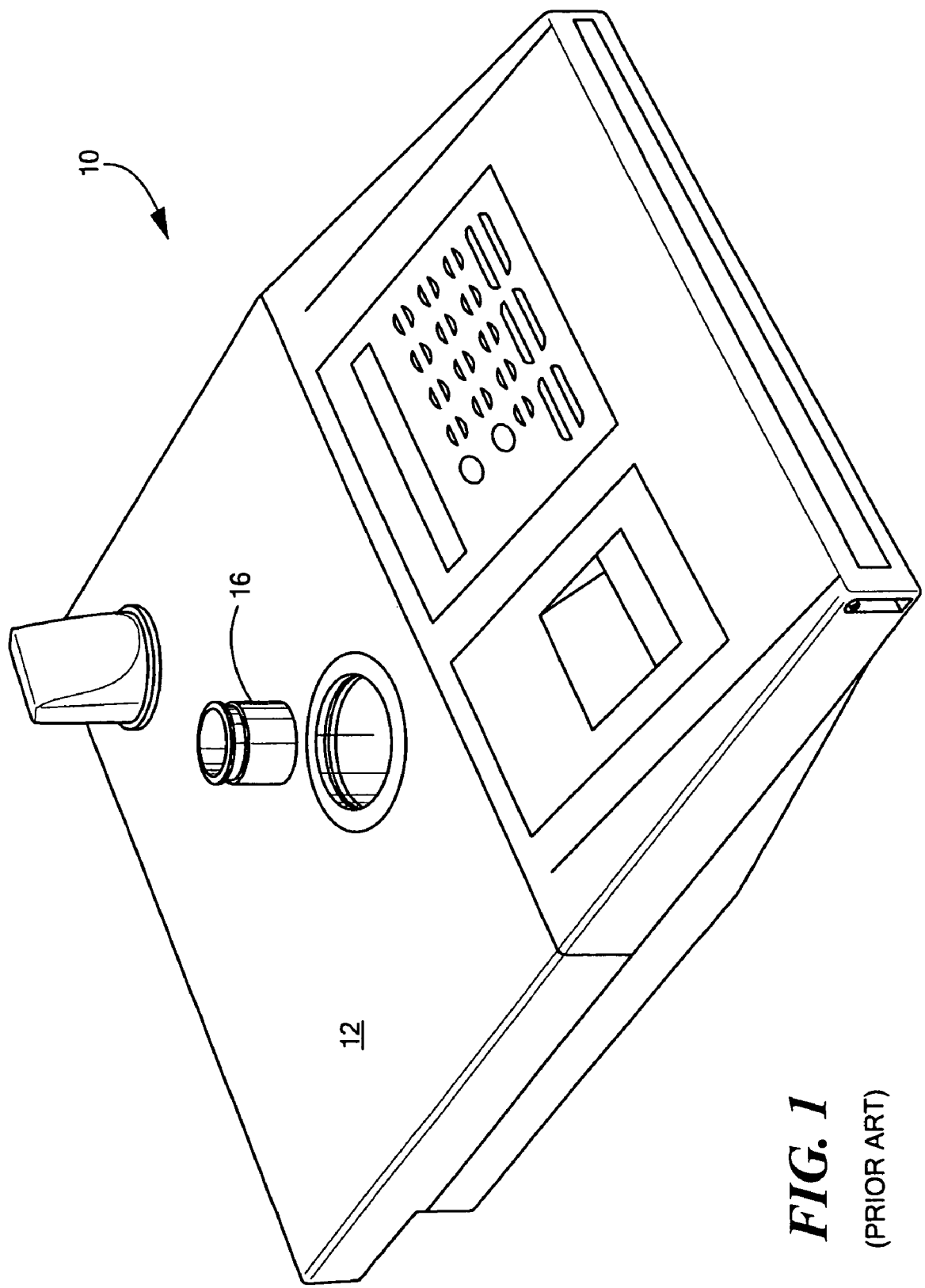
FIG. 1 is a schematic three-dimensional depiction of a typical prior art XRF system for analyzing fuel and oil samples on board a marine vessel.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

As discussed in the Background section above, a conventional x-ray fluorescence system 10, FIG. 1 includes an analyzer 12 into which is placed sample cup 16. If cup 16 breaks or tips, or if the sample spills out of the open end of cup 16, the sample can contaminate the x-ray source, the detector, and/or the electronic analyzer and other components housed within unit 12.

Figure 2:
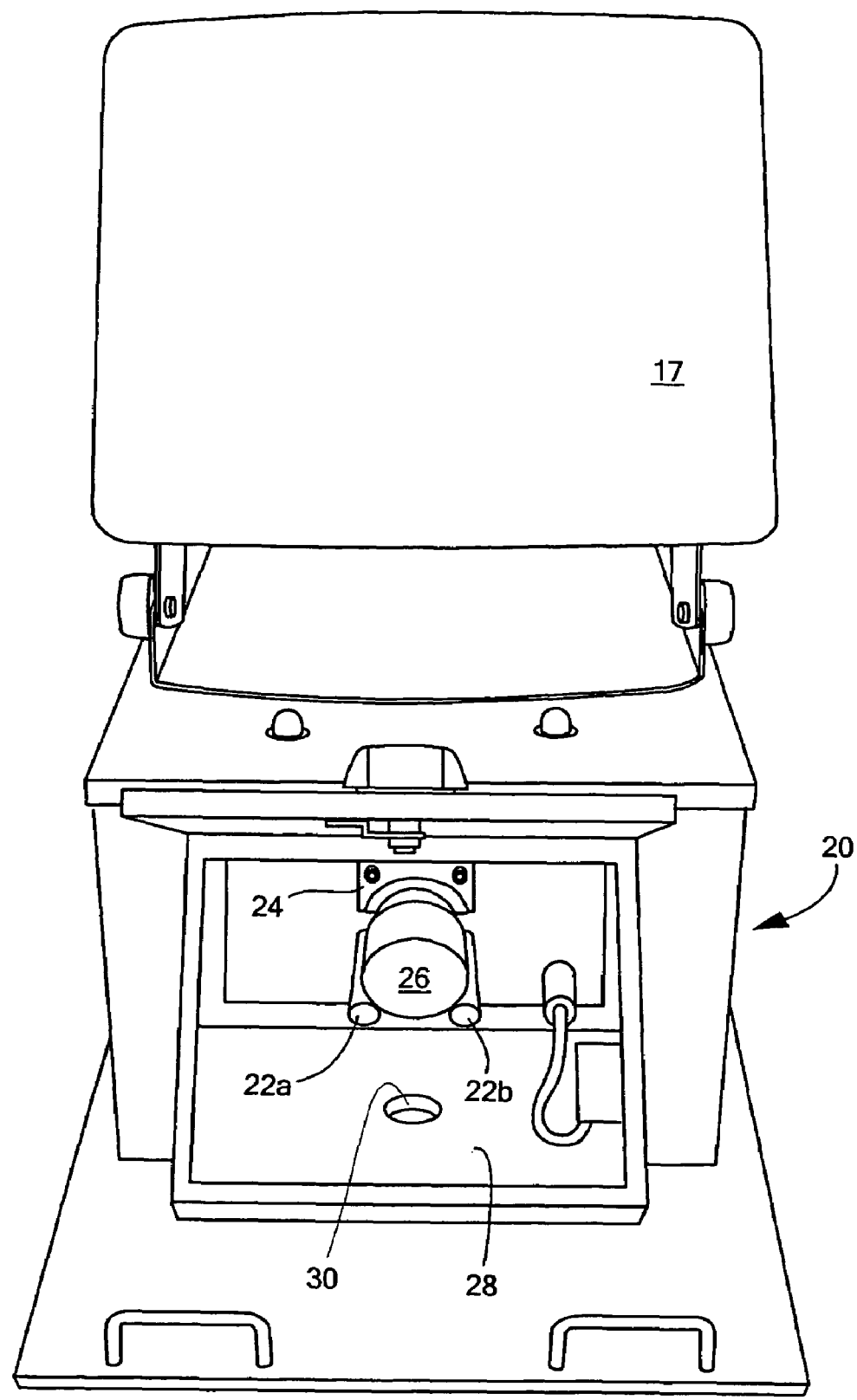
FIG. 2 is a schematic three-dimensional view showing an embodiment of an XRF system in accordance with the subject invention.
Figure 3:
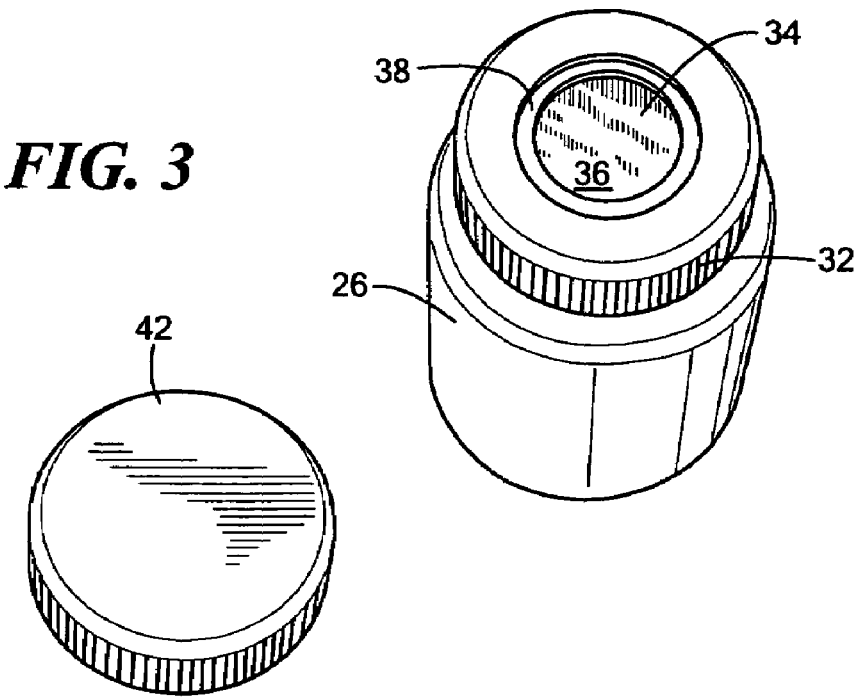
FIG. 3 is a schematic three-dimensional top view showing one preferred embodiment of a sample bottle fitted with the windowed cap and also showing a separate regular cap.
Figure 4:
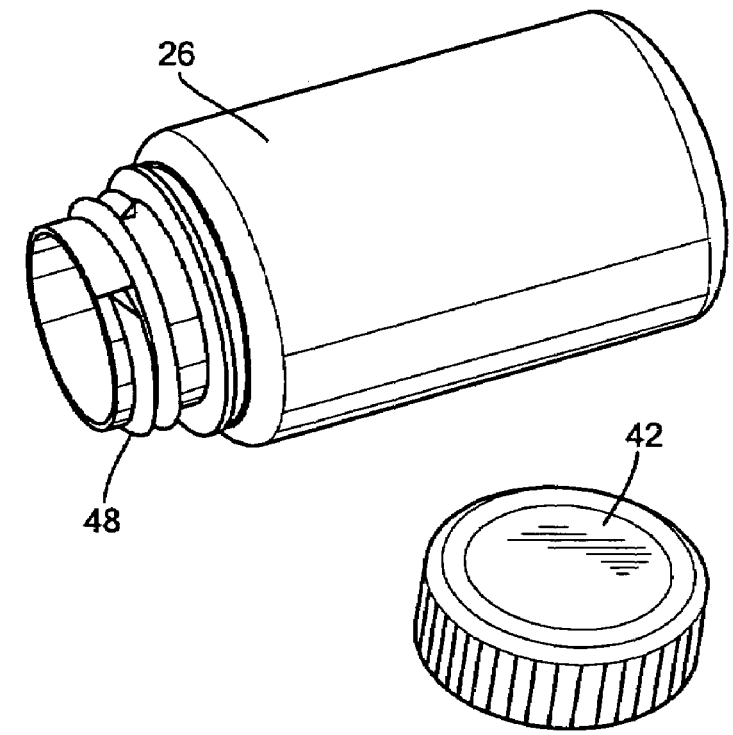
FIG. 4 is a schematic three-dimensional exploded front view of the sample bottle and windowed cap combination shown in FIG. 3.
Figure 5:
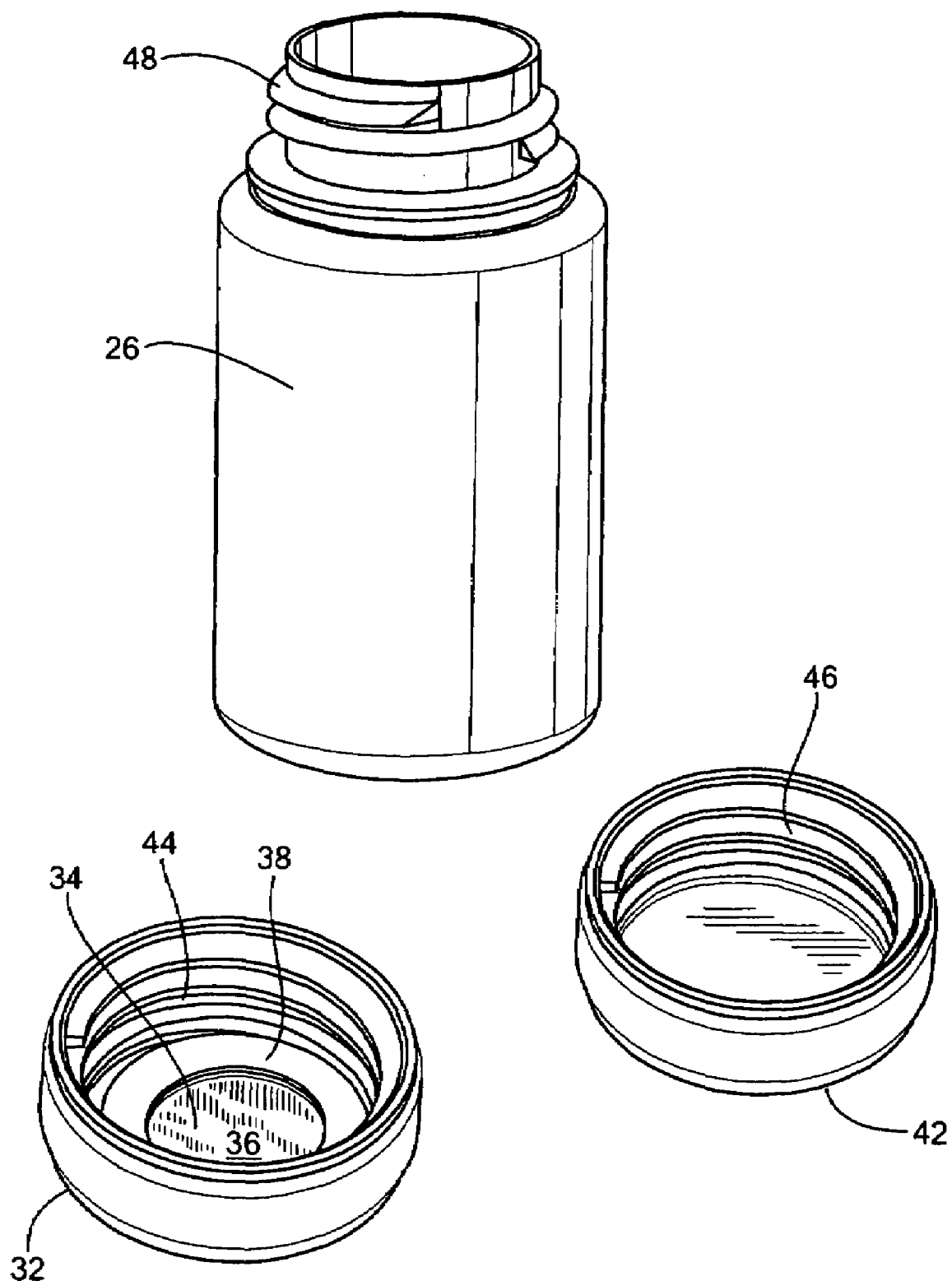
FIG. 5 is a schematic three-dimensional front view again showing the preferred sample bottle and two different types of bottle caps which can be fitted on to the sample bottle in accordance with the subject invention.
Figure 6A:
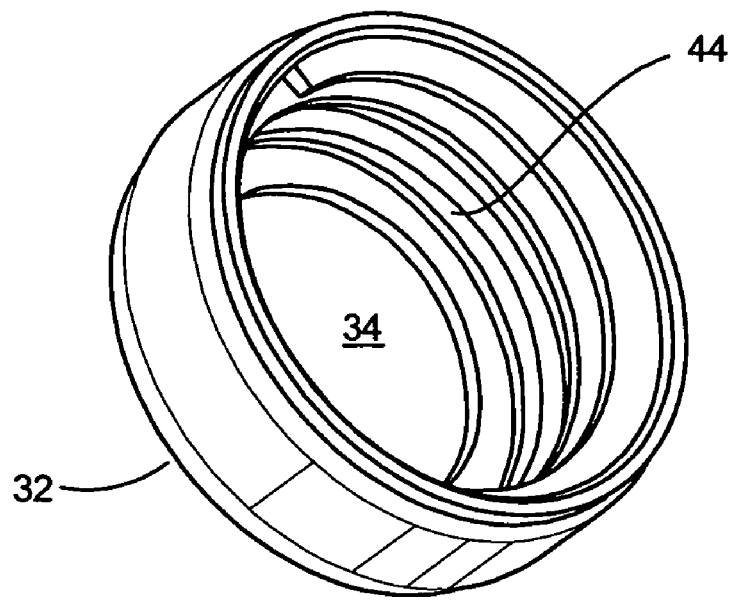
FIGS. 6A-6B are schematic views showing a preferred version of a windowed cap.
Figure 6B:
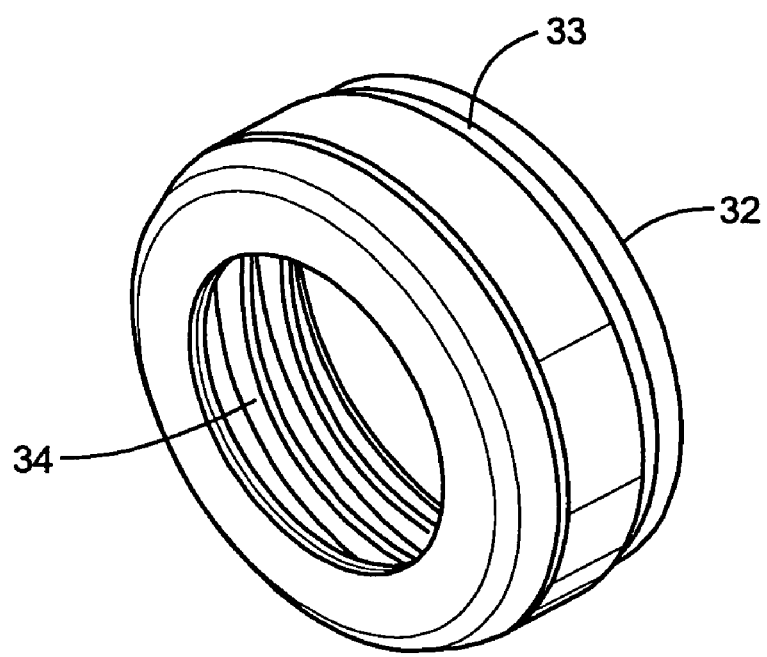
Figure 7:
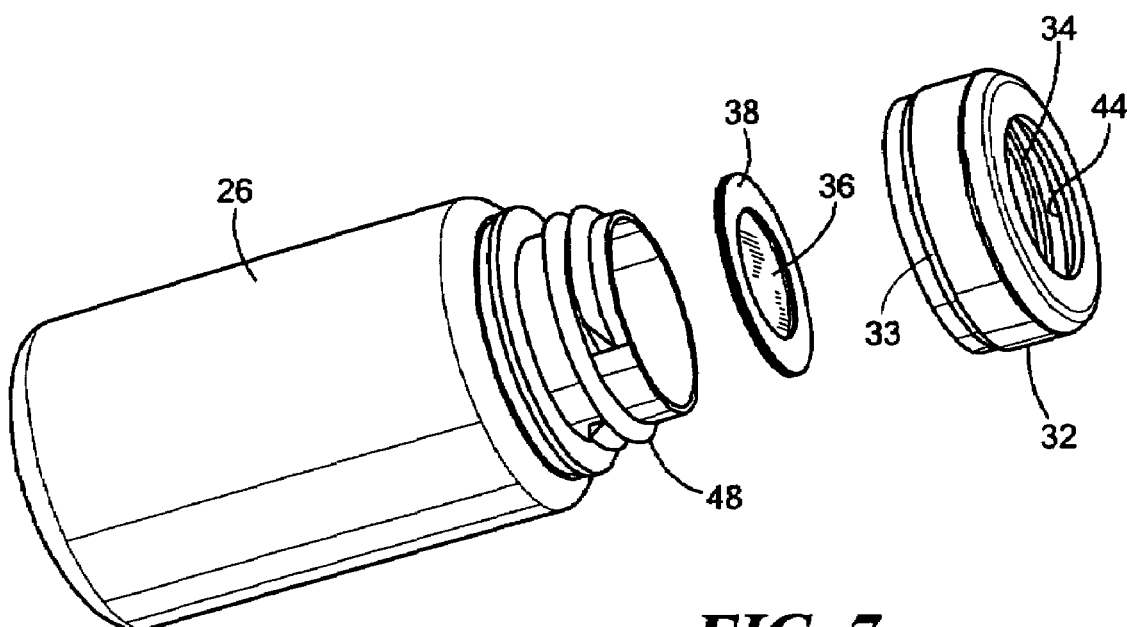
FIG. 7 is another schematic view of a sample bottle in accordance with the subject invention.
Figure 8:
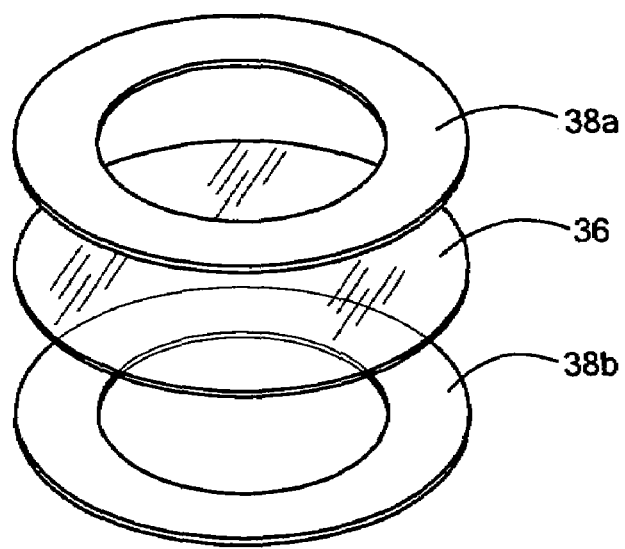
FIG. 8 is a schematic view of the Kapton cap window.

XRF system 20, FIG. 2, in accordance with one preferred embodiment of the subject invention is more robust and rugged. A sample bottle holder including posts 22a and 22b and sample bottle adapter 24 positions novel sample bottle 26 horizontally with respect to unit 20. Should spillage occur, gravity will force the sample to flow down onto tray 28 with gravity drain 30. In this way the x-ray source, the detector, and the other electronic components within unit 20 will not be contaminated by inadvertent spills.

FIGS. 3-8 show a preferred version of sample bottle 26 in more detail. Typically, a supply of such sample bottles is available to the user of system 20, FIG. 2. Each sample bottle 26, e.g., a 125 ml bottle, includes first plastic cap 32 with window 34 therein for allowing x-rays to pass into and out of the sample bottle when it is mounted in the holder of analyzer 20, FIG. 2. The window preferably includes Kapton film 36, e.g., 0.3 mils thick, surrounded by paper gasket 38 receivable under cutout opening 40, FIG. 4 in cap 32. Second cap 42 is standard in design and has no window and can be used to store and transport a sample in bottle 26 after analysis. Both caps typically include internal threads (threads 44, FIG. 5 for windowed cap 32 and threads 46 for regular cap 42) which cooperate with external threads 48 on bottle 26. Materials other than Kapton may be used for the window provided the material used is chemically resistant to the material placed in the sample bottle and also allows efficient transmission of x-rays typically from 1 keV upwards.

Cap 32 is designed to replace the standard storage cap of the 125 ml Nalgene bottle. It has a thinner, flatter profile than the standard cap to place the sample window closer to the measurement probe and internal features to ensure a tight seal and proper alignment of the window with respect to the bottle. The exterior of the cap features a radiused groove 33 designed to interlock with the bottle capture feature of the measurement system. After filling the sample bottle with liquid under test, the Kapton window assembly is placed on the bottle lip. The sample window cap is then screwed in place, capturing the window against the bottle lip and providing a leak-proof seal and Kapton testing window. The Kapton window assembly includes of a disk of 0.3 mil Kapton Polyamide film 36 sandwiched between two die-cut 15-point thick cardboard rings 38a and 38b. The cardboard is self adhesive on one side (interior faces) and the inner diameter of the cardboard window is die cut prior to assembly while the outer diameter is die cut post assembly. This approach allows the Kapton window to extend to the edges of the assembly allowing it to act as both window and leak-proof seal. The assembly is designed to seat on the perimeter lip of the sample bottle and be captured between it and the sample window lid. The sample bottle and Kapton window in testing withstood liquid up to 120° C. without leakage or distortion.

Figure 9A:
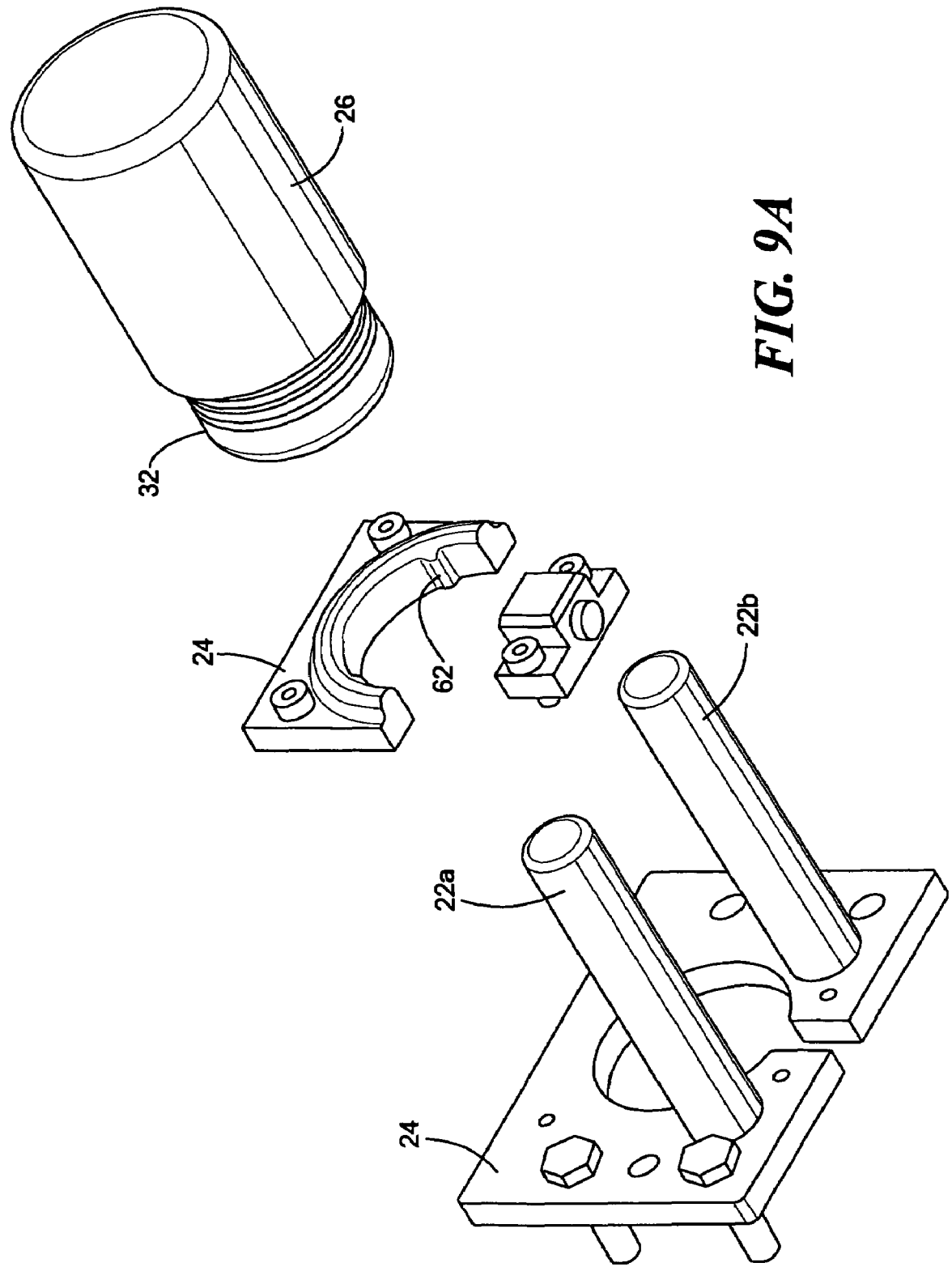
FIGS. 9A-9B are schematic views showing an example of a bottle holder in accordance with the subject invention.
Figure 9B:
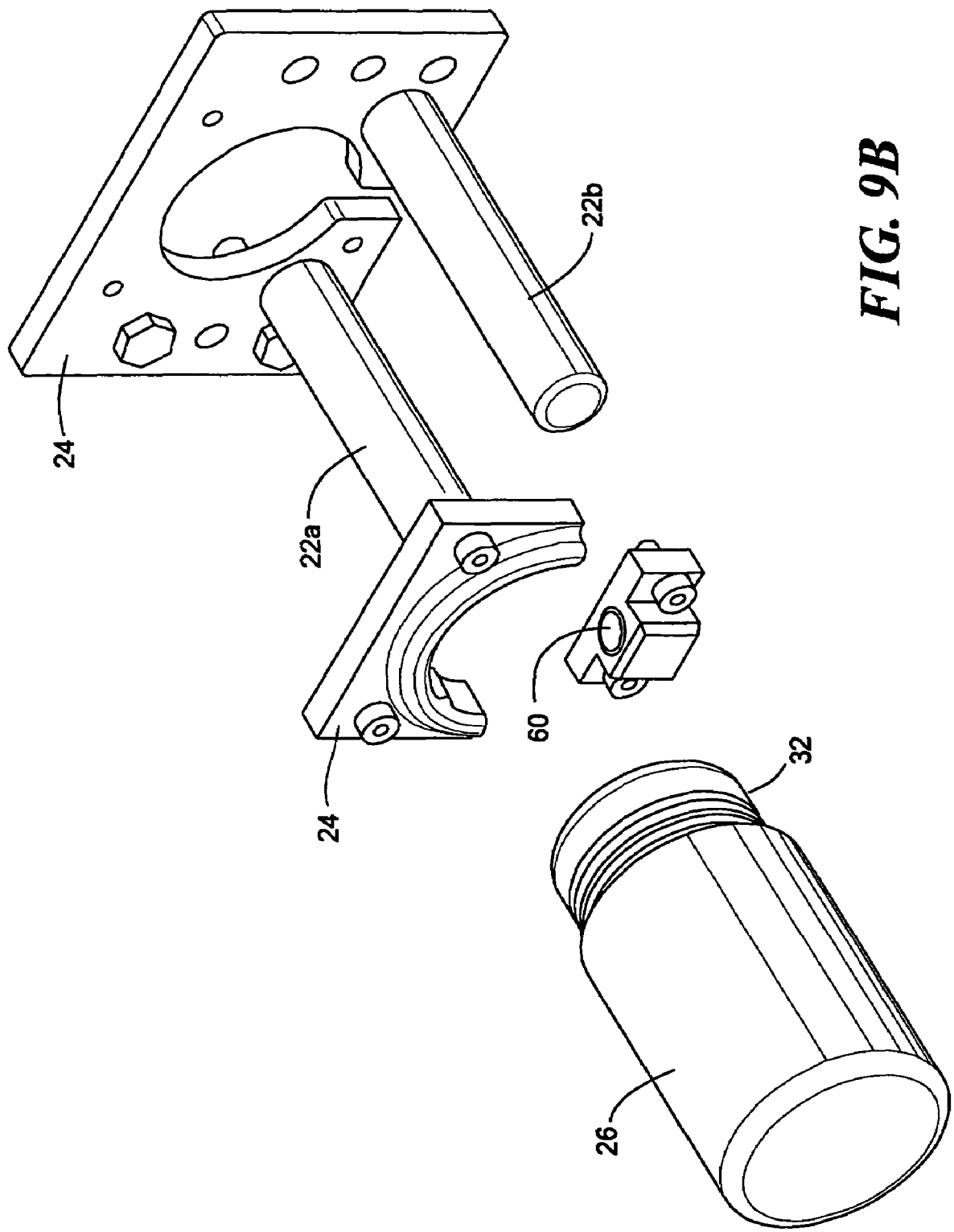
Figure 10:
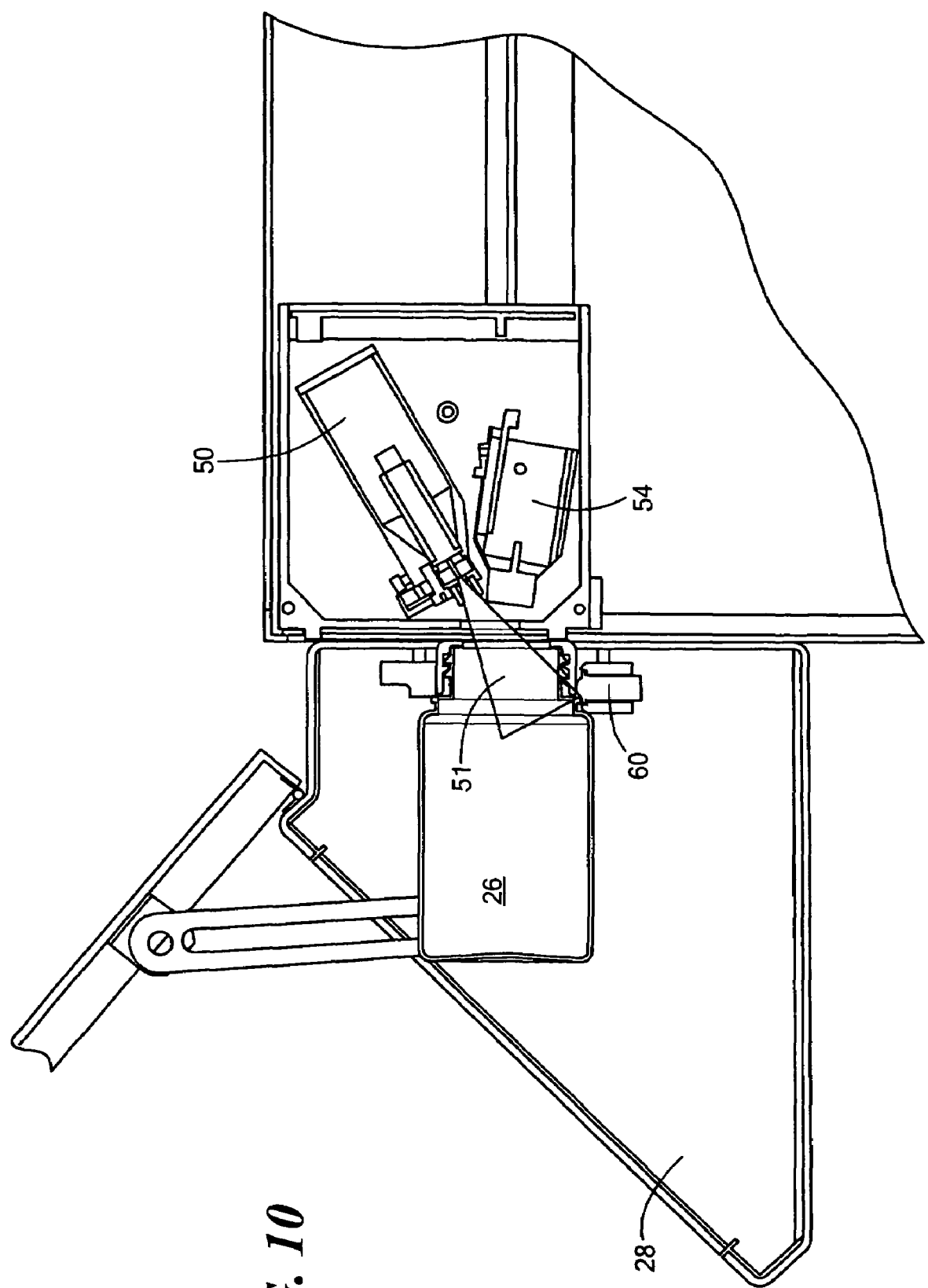
FIG. 10 is a schematic sectional view showing several of the primary components associated with the XRF analyzer of FIG. 2.

FIGS. 9-10 show the primary components associated with a typical analyzer unit 20. X-ray source 50 emits x-rays 51 directed through the sample bottle adapter and into bottle 26 through window 34, FIG. 3 in cap 32. X-rays emitted by the sample (fuel, oil, other liquids, loose powders, etc.) in the bottle pass back through window 34 and are directed to detector 54. After a sample is analyzed (a typical unit includes readout screen 17, FIG. 2 and printing capability), cap 32, FIG. 3 can be removed and cap 42 installed for storage and/or transport of the sample in bottle 26. In the preferred example, bottle 26, FIGS. 9-10 is retained in the system by a spring loaded ball plunger 60 engaged with radiused groove 33 in the cap of the bottle. Guide features 62 in the retainer apparatus 24 maintain the orientation of the bottle with respect to the XRF components. Additional posts may be provided. Also, the sample bottle holder may vary in design in accordance with the subject invention.

The result in any embodiment is a more robust and rugged XRF system which prevents spillage onto the sensitive internal components of x-ray analyzer unit 20. By providing both a windowed cap and a regular cap, collection, transport, analysis, and storage of a sample require only a single container bottle. Such a system is thus easier to use and more ergonomic in design. The system can be used on board marine vessels or in any environment where a more rugged XRF system is desired.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. An XRF system comprising:
    an analyzer including:
        a sample bottle holder configured to receive a horizontally disposed sample bottle and including a member which engages the sample bottle;
        an x-ray source positioned to emit x-rays into a sample bottle placed in the holder, and
        a detector positioned to receive x-rays emitted by a sample in the sample bottle positioned in the sample bottle holder; and
    a supply of sample bottles receivable horizontally in the sample bottle holder, each sample bottle including:

a first cap with the window therein for allowing x-rays to pass therethrough when the sample bottle is positioned horizontally in the holder, and a second cap without a window for transporting and storing the sample vertically; and a tray beneath the sample bottle holder for catching a sample spilled from the horizontally disposed sample bottle.

2. The system of claim 1 in which the window includes a film surrounded by a gasket receivable under an opening in the cap.

3. The system of claim 2 in which the film is made of plastic.

4. The system of claim 1 in which the bottle and the caps are made of plastic.

5. The system of claim 1 in which the sample bottle holder member is biased to engage the first cap.

6. The system of claim 5 in which the first cap includes a radiused capture feature designed to interlock the first cap with the sample bottle holder via the biased member.

7. An XRF analyzer sample container system comprising:

a bottle for holding a sample to be analyzed by an XRF analyzer;

a first cap for an open end of the bottle including a window for allowing x-rays to pass therethrough when the sample bottle is placed in the XRF analyzer; and a second cap for the open end of the bottle without a window for transporting and storing the sample.

8. The system of claim 7 in which the window includes a film surrounded by a gasket receivable under an opening in the cap.

9. The system of claim 8 in which the film is made of plastic.

10. The system of claim 7 in which the bottle and the first and second caps are made of plastic.

11. The system of claim 7 in which the first cap includes a radiused capture feature.

12. An XRF system comprising:

an analyzer including:

a sample bottle holder on a side of the analyzer;

an x-ray source positioned to emit x-rays into a sample bottle placed in the holder, and a detector positioned to receive x-rays emitted by a sample in the sample bottle positioned in the sample bottle holder; and a supply of sample bottles receivable in the sample bottle holder, each sample bottle including:

a first cap with the window therein for allowing x-rays to pass therethrough when the sample bottle is positioned in the holder, and a second cap without a window for transporting and storing the sample.

* * * * *